United States Patent [19]

Martin et al.

[11] Patent Number: 5,082,141
[45] Date of Patent: Jan. 21, 1992

[54] DEVICE FOR SINGULATING PARTICLES

[75] Inventors: Charles R. Martin; Robert Rousser; Daniel L. Brabec, all of Manhattan, Kans.

[73] Assignee: The United States of America as represented by the Secretary of Agriculture, Washington, D.C.

[21] Appl. No.: 519,195

[22] Filed: May 3, 1990

[51] Int. Cl.$^5$ .............................................. B65G 59/00
[52] U.S. Cl. .................................. 221/278; 221/203; 221/211; 221/277; 432/105
[58] Field of Search ............... 221/200, 203, 211, 217, 221/222, 231, 237, 258, 265, 277, 278; 34/134; 432/105

[56] References Cited

U.S. PATENT DOCUMENTS

| | | | |
|---|---|---|---|
| 3,245,154 | 4/1966 | Bojner et al. | 34/134 X |
| 3,741,717 | 6/1973 | Triplett | 432/105 |
| 3,860,146 | 1/1975 | Bauman et al. | 221/211 |
| 3,900,131 | 8/1975 | Ehrlich | 221/278 X |
| 4,148,414 | 4/1979 | Parks, Jr. | 221/278 |
| 4,516,690 | 5/1985 | Andersson | 221/278 X |
| 4,898,564 | 2/1990 | Gunn et al. | 221/211 X |

OTHER PUBLICATIONS

Y. Pomeranz et al., "Wheat Hardness Determined by a Single Kernel Compression Instrument with Semiautomated Feeder," Cereal Chem. 65(2): 86–94 (1988).

Primary Examiner—H. Grant Skaggs
Assistant Examiner—Tuan N. Nguyen
Attorney, Agent, or Firm—M. Howard Silverstein; John D. Fado; Curtis P. Ribando

[57] ABSTRACT

A feeding device singulates, orients, and delivers seeds and other comparatively smooth-surfaced particulate material to a desired destination. The device comprises a horizontal rotating drum having an inner surface cut with a spiral groove for orienting ellipsoid-shaped particles and advancing them to the location of pickup orifices within the drum. A vacuum valve alternately subjects the orifices to vacuum and ambient pressure for picking up the individual particles and releasing them to the desired point of delivery.

4 Claims, 2 Drawing Sheets

DEVICE FOR SINGULATING PARTICLES

CROSS-REFERENCE TO RELATED APPLICATION

This invention is related to commonly assigned application P. C. 2007.90 of Martin et al. entitled "Rapid, Single Kernel Grain Characterization Device," Ser. No. 519,196, now U.S. Pat. No. 5,005,774, filed concurrently herewith on May 3, 1990.

BACKGROUND OF THE INVENTION

1. Field of the Invention

New technologies that require singularizing of seeds for objective evaluation are being developed to aid grain inspectors in the grading of grain. Examples of new technologies for single-seed evaluation include computerized analysis of weight, moisture, hardness, and digitized image video measurements. Grain market samples are frequently mixtures of the same kind of seed from different varieties and growing conditions. Seed mixtures can have a wide diversity in their size and shape.

This invention relates to an apparatus and method useful for singulating seeds from a sample composed of mixtures of sizes and shapes. The apparatus and method deliver the seeds in proper orientation to some predetermined destination at predetermined time intervals. The invention would be especially useful in the developing technologies that require single-seed metering.

2. Description of the Prior Art

Technology for metering singulated seeds has been developed by manufacturers of agricultural equipment used to plant crops. Crop seeds are a single variety and are frequently processed to uniform size for maximum handling efficiency.

Pomeranz et al. [Cereal Chem. 65(2): 86-94 (1988)] show a semiautomated feeder device for use with a single kernel compression instrument for grains of wheat. The device requires that wheat kernels be manually singulated and pushed down a slide to a set of action surfaces. As the feeder passes each seed over the surfaces, the kernel becomes oriented with the crease downward. The feeder then positions the kernel on the crushing surface of the compression instrument while simultaneously brushing away the previously crushed kernel.

SUMMARY OF THE INVENTION

We have now discovered a feeding device for singulating seeds and other comparatively smooth-surfaced particulate material, and thereafter delivering the singulated material to some predetermined destination. This novel feeder comprises:

a drum adapted to hold a plurality of the kernels and to rotate horizontally about its axis and having an inner surface and an outer surface, wherein the inner surface has a spiral groove extending at least a portion of the length of the inner surface and terminating in a concentric groove near one end of the drum;

at least one orifice in the concentric groove having a dimension substantially smaller than one of the kernels;

a means for applying a vacuum to the orifice during the time that the orifice rotates in a circular path from a first predetermined position which is below the axis of the drum to a second predetermined position which is above the first position, whereby a single kernel positioned over the orifice during the time the vacuum is applied will be retained over the orifice;

means for releasing the vacuum when the orifice is positioned at a third predetermined position which is above the first position, whereby the single kernel will be released from the orifice;

means for directing the released kernel to the predetermined destination.

In accordance with this discovery it is an object of the invention to provide an automated means for singulating individual seeds or other grain-like particulate material from a bulk quantity of the material and delivering each singulated seed or material to some final destination or to some stage of an operation for subsequent treatment or processing.

Another object of the invention is to orient biaxially symmetrical grains along a preselected one of the axis for purposes of delivery in a uniform fashion to the destination.

It is also an object of the invention to provide a feeding device which is rapid, inexpensive, reliable, and which consistently delivers singulated material to its destination in proper orientation.

A further object of the invention is to provide a design for a feeder device which is readily adaptable to any of a wide diversity of seeds and other similar smooth-surfaced, particulate materials.

Other objects and advantages of the invention will become readily apparent from the ensuing description.

Detailed Description of the Invention

The feeder device of this invention is useful for singulating and orienting a variety of particulate materials to include cereal grains and other seeds. It is also useful with other generally spheroid or ellipsoid particles, particularly those which have a sufficiently smooth surface to form a vacuum seal with the device as described below. Examples of such other particles include pills, capsules, insert eggs, and the like. The terms "particle" and "material" used in the ensuing discussion are intended to refer to any materials of this nature.

Figure 1:
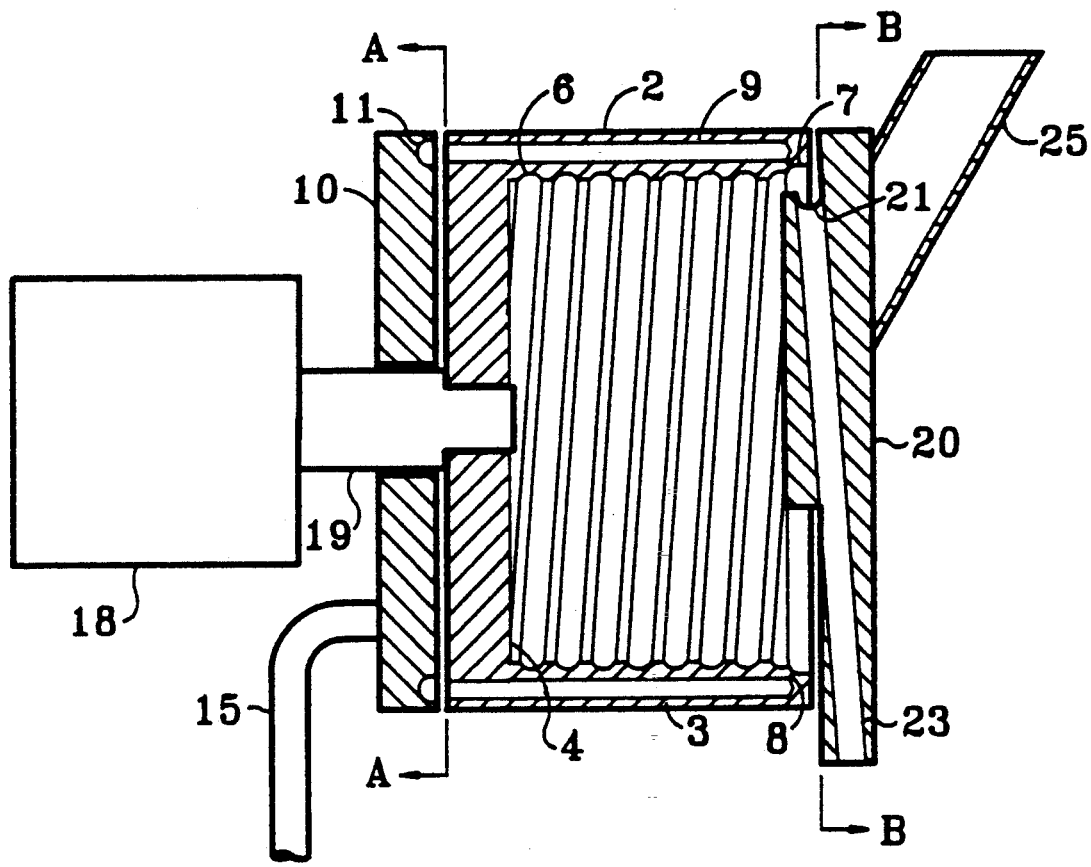
FIG. 1 is a partially cut-away front view of the feeder device.

As illustrated in FIG. 1, the feeding device 1 of the invention essentially comprises a drum 2 having cylindrical side wall 3, base 4, fixed base plate 10, and fixed face plate 20. The axis of the drum is oriented horizontally, and the drum is driven by motor 18 about the horizontal axis. Motor shaft 19 extends through the center of fixed base plate 10 which is rigidly mounted with respect to the motor so that the mating surfaces of base 4 and plate 10 produce a tight fit. Hopper 25 is provided to charge the drum with the material to be singulated.

A portion of the inner surface of side wall 3 is cut with a spiral groove 6 which terminates with concentric groove 7 near the face plate 20. For best results, the cross section of grooves 6 and 7 is U-shaped, and the transverse dimension should approximate that of the particles of material. Biaxially symmetrical particles will thereby tend to become oriented longitudinally within the grooves. Spiral groove 6 preferably extends along the full length of the inner surface so that all material which is charged into the drum via hopper 25 will ultimately be conveyed to concentric groove 7. It is understood that the direction of drum rotation is selected to promote advancement of the material toward the concentric groove.

Concentric groove 7 is provided with one or more orifices 8 which are appropriately sized relative to the material to be singulated as described in further detail below. If a plurality of orifices are provided, they should be evenly spaced about the circumference of groove 7 so that the singulated particles will be fed out by the device at regular intervals. Each orifice is in communication with a drilling 9 which extends through side wall 3 and base 4.

Figure 2:
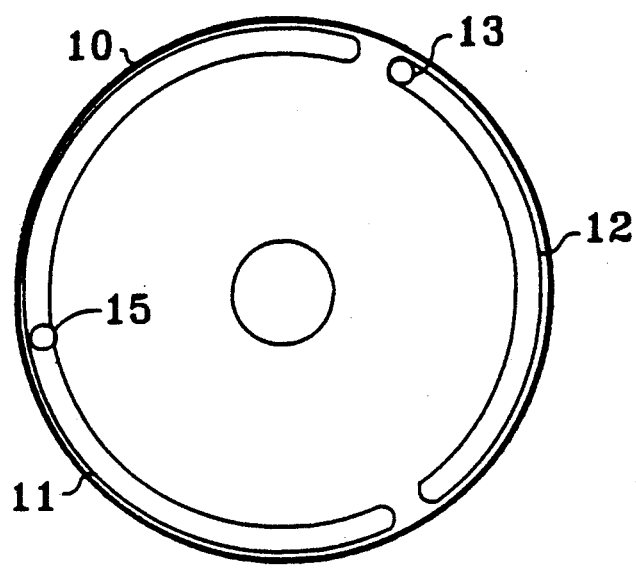
FIG. 2 is a sectional view along lines A—A of FIG. 1.

As best shown in FIG. 2, fixed base plate 10 houses the means for valving a vacuum to drillings 9. In a preferred design, channel 11 connected to a vacuum source 15 is configured to communicate with each orifice 8 as it rotates in a circular path from some first predetermined point below the drum axis to some second predetermined point above the drum axis. Channel 12 communicates with the ambient or some positive pressure source through port 13. Channel 12 is preferably configured to communicate with each orifice 8 as it rotates from a third predetermined point above the drum axis to a fourth predetermined point intermediate to the third and first points. Thus, as drum 2 rotates, vacuum is alternately valved ON and OFF to drillings 9 and orifices 8. A grease seal or other tight-fitting arrangement between base 4 and base plate 10 is necessary to insure the appropriate pressure at the orifice at a given time.

In operation, the material to be singulated is charged into drum 2 through hopper 25. The amount of the material should fill no more than about 10-20% of the drum volume. As the drum rotates, particles of the material become aligned within the spiral groove 6 and are conveyed to concentric groove 7. The force of gravity tends to keep the material near the bottom of the drum. When an orifice under vacuum sweeps under a particle in groove 7, suction forces secure the particle over the orifice. The particle is thereby retained over the orifice as it rotates above the axis of the rotating drum, whereas other particles within the groove remain near the bottom. As drilling 9 comes into communication with channel 12, the vacuum is broken and the particle is released.

Figure 3:
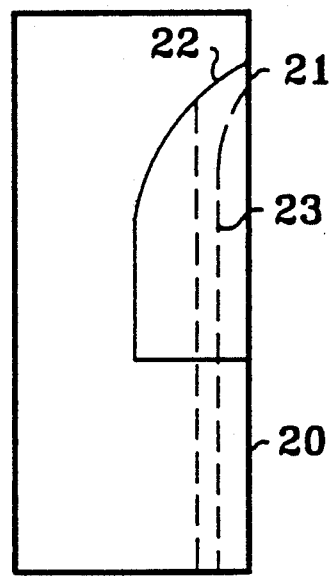
FIG. 3 is a sectional view along lines B—B of FIG. 1.

The particle released from the orifice in the concentric groove is delivered to the next stage of processing or to its final destination by means of a guide. The guide may assume any of a variety of configurations. The embodiment shown in FIGS. 1 and 3 is specifically designed to maintain the orientation of a substantially biaxially symmetrical particle such as a grain of wheat or rice. Face plate 20 is provided with opening 21 to arcuate channel 22. The opening is positioned in close proximity to the point of release of the particle from the orifice 8 and is in approximately the same plane as concentric groove 7. Arcuate channel 22 has a curvature which approximates the natural trajectory of the released particle resulting from the momentum imparted by the drum as affected by the force of gravity. As the horizontal component of the trajectory becomes insignificant with respect to the vertical component, the particle is then easily diverted to a different plane of descent, such as by the linear channel 23 shown in FIGS. 1 and 3.

By virtue of a constant speed of rotation of drum 2 and a constant spacing between orifices 8, the device can very precisely meter the singulated particles at regularly spaced intervals. In tests with kernels of wheat, up to 200 kernels per min have been singulated. Selection of the groove size, orifice size, vacuum pressure, and rate of drum rotation according to the particular application would be within the skill of a person in the art.

It is understood that the foregoing detailed description is given merely by way of illustration and that modification and variations may be made therein without departing from the spirit and scope of the invention.

We claim:

1. A feeder for singulating kernels of grain or grain-like materials and for feeding the singulated kernels to a predetermined destination comprising:

a drum adapted to hold a plurality of the kernels and to rotate horizontally about its axis and having an inner surface defining the interior of the drum and an outer surface, wherein the inner surface has a spiral groove extending at least a portion of the length of the inner surface and terminating in a concentric groove near one end of the drum;

at least one orifice in the concentric groove having a dimension substantially smaller than one of the kernels;

a means for applying a vacuum to the orifice from a vacuum source during the time that the orifice rotates in a circular path from a first predetermined position which is below the axis of the drum to a second predetermined position which is above the first position, where by said vacuum source is positioned exterior to the drum and is in communication with the interior of the drum only through the orifice, and whereby a single kernel positioned over the orifice during the time the vacuum is applied will be retained over the orifice;

means for releasing the vacuum when the orifice is positioned at a third predetermined position which is above the first position, whereby the single kernel will be released from the orifice;

means for directing the released kernel to the predetermined destination.

2. A feeder as described in claim 1 and further comprising a hopper for introducing the kernels into the drum.

3. A feeder as described in claim 1 wherein the means for applying a vacuum and the means for releasing a vacuum is a vacuum valve, whereby the orifice is in communication with a vacuum source when it is at, or intermediate to the first and second predetermined positions, and the orifice is in communication with the ambient when it is positioned at, or intermediate to, the third and a fourth predetermined position.

4. A feeder as described in claim 1 wherein the means for directing the released kernel is a guide which has a shape corresponding with the natural trajectory of the released kernel imparted by the rotating drum.

* * * * *